United States Patent [19]

Romanovskaya

[11] Patent Number: 4,653,506
[45] Date of Patent: Mar. 31, 1987

[54] METHOD OF INDIRECT MEASUREMENT OF ARTERIAL TENSION AND A DEVICE FOR PULSE WAVE REGISTRATION

[75] Inventor: Antonina M. Romanovskaya, Moscow, U.S.S.R.

[73] Assignee: Vsesojuzny Nauchno-Issledovtelsky i Ispytatelny Institut Meditsinskoi Tekhniki, U.S.S.R.

[21] Appl. No.: 527,802

[22] Filed: Aug. 30, 1983

Related U.S. Application Data

[63] Continuation-in-part of Ser. No. 165,659, Jul. 3, 1980, abandoned.

[30] Foreign Application Priority Data

Jul. 5, 1979 [SU] U.S.S.R. ............................... 2778002

[51] Int. Cl.[4] ............................................... A61B 5/02
[52] U.S. Cl. ................................... 128/677; 128/686; 128/687
[58] Field of Search ................. 128/677, 686, 691–692, 128/687–690; 73/861.18–861.19

[56] References Cited

U.S. PATENT DOCUMENTS 2,658,505 11/1953 Sheer .................................... 128/687
3,154,066 10/1964 Grindheim et al. ................ 128/687
3,315,662 4/1967 Buffington ........................... 128/687
3,903,873 9/1975 Royal et al. ...................... 128/688 X
4,409,983 10/1983 Albert .................................. 128/690

Primary Examiner—Kyle L. Howell
Assistant Examiner—Angela D. Sykes
Attorney, Agent, or Firm—Steinberg & Raskin

[57] ABSTRACT

In a method of indirect measurement of arterial tension, a compression cuff is applied to the surface of a patient's body and the pressure in the cuff is varied within a range which covers the systolic and diastolic values of the arterial pressure. As the pressure in the cuff is varied, a change in the magnitude of the angle between the surface of the patient's body and the direction of propagation of the blood pulse wave under the cuff is monitored. The instants when the blood pulse wave appear and disappear are registered by the magnitude of said angle. The pressure effective in the cuff is measured at said instants. The angle between the surface of the patient's body and the direction of propagation of the pulse waves is measured by a device for registering the passing of the pulse waves. The device comprises a housing, a pellet accommodated in the housing with a possibility of oscillating about the pivot axis, said pellet having a contact surface, and a transducer converting oscillations of the pellet into electric signals.

12 Claims, 16 Drawing Figures

METHOD OF INDIRECT MEASUREMENT OF ARTERIAL TENSION AND A DEVICE FOR PULSE WAVE REGISTRATION

The present Application is a continuation-in-part of Application Ser. No. 165,659 filed on July 3, 1980, and now abandoned.

BACKGROUND OF THE INVENTION

The present invention relates to medical engineering. More particularly the invention relates to a method of indirect measurement of arterial tension and a device for pulse wave registration.

The invention will find most widespread application in indirect determination of patient's arterial tension at an increased ambient noise level, and at an increased level of noise produced by patient's motions.

One prior-art method of measuring arterial tension with the aid of a compression cuff and a sensor of the Korotkov sounds (cf. "Acoustic method of arterial tension examination" by G. I. Kositsky, Medgiz PH, Moscow 1959, pp. 53-54 (in Russian) includes the application of a compression cuff to the surface of the patient's body. The pressure in the cuff is varied within a range covering the systolic and diastolic values of the patient's arterial tension and the Korotkov sounds produced by the arterial pulse waves issuing from under the cuff are simultaneously registered via a microphone, said values corresponding to the instants when the Korotkov sounds appear and disappear.

However, the aforesaid method is disadvantageous because the microphone picks up not only the Korotkov sounds, but also ambient noise, and in some cases it fails to measure the arterial tension value when the measurement process is automated, since the loudness of the Korotkov sounds, their spectral composition and some other characteristics are substantially different in every patient.

A more perfect method of measuring the arterial tension, capable of more accurate determination of the extreme values of such tension is a known method, which is based upon registration of a pulse wave and is insensitive to ambient noise. This method includes the application of a compression cuff to the surface of the patient's body. The pressure in the cuff is varied within a range which covers the systolic and diastolic values of arterial tension and pulse waves resulting from the releasing of the artery compressed by the cuff are registered. The pressure in the cuff is measured at the instants when these pulse waves appear and disappear. The pulse waves are registered under the cuff on the body surface area located opposite the artery and beyond the midpoint of the cuff as along the direction of the arterial blood flow, against displacement of the surface of the patient's body in a direction square with that surface (cf. "Automatic meter for indirect measurement of arterial tension" by V. M. Bolshov et al., "Medtekhnika", No. 2, 1979, pp. 19-22 (in Russian).

However, the aforedescribed method is disadvantageous in that the accuracy of measurement of the systolic and diastolic arterial pressures is too low. This disadvantage stems from the fact that the aforesaid displacement of the patient's body surface in a direction square with that surface may occur without any pulse waves passing under the cuff, that is, without releasing the artery, but may result from pressure fluctuations in the cuff which are liable to arise usually before releasing the compressed artery, or from muscular contractions of the body portion located under the cuff, or else it may be caused by elastic deformation of the walls of the filled artery when the pressure in the cuff is below the diastolic value.

It becomes evident from the diagrams obtained from determining the arterial tension by the known method that the signals resulting from the noise, e.g., due to the patient's muscular contractions have an amplitude much greater than that of the useful signals produced by the blood pulse waves. This results in that a signal is registered from the noise alone, without any pulse wave passed, which in turn leads to incorrect readings of the arterial tension values.

The heretofore-known device for registering blood pulse waves in indirect measurement of arterial tension (cf. USSR Inventor's Certificate Ser. No. 651,786, class A61B 5/02 dated 1979) comprises a housing and a transducer rigidly secured to the housing, said transducer being adapted to convert mechanical motions into electric signals. A pellet is secured to the transducer traversable portion, said pellet having a contact surface and being adapted to impart to said transducer the displacements of the patient's body surface square with said surface and hence with the pellet contact area.

The transducer is in effect a disk-shaped piezocrystal and the pellet, also disk-shaped and made from a hard material such as plastic, located at the central axis of the transducer.

The known device is arranged under the compression cuff past its midpoint in the direction of the blood flow.

However, the aforedescribed device fails to provide high-accuracy measurement of the systolic and diastolic values of arterial tension, since it is sensitive to pressure oscillations in the cuff and to motions of the body surface due to muscular contractions. Thus for instance, when measuring arterial tension under decompression conditions, pressure oscillations arise in the cuff before a first pulse wave passes under the cuff, from which the systolic value of the arterial tension is measured. These pressure oscillations create a force which is exerted on the housing of the device to cause mutually opposite displacements of the housing and pellet. This results in a false signal appearing at the output indicating the passing of a pulse wave, and in a mismeasured systolic value of the arterial tension. The pellet is displaced in the same manner due to muscular contractions under the device occurring at a pressure in the cuff below the diastolic value and due to an elastic pulsing deformation of the walls of filled artery with the resultant false signals at the output of the known device. All this leads to inaccurate determination of the systolic and diastolic values of the arterial tension and renders it impossible to measure arterial tension with the patient moving.

SUMMARY OF THE INVENTION

The principal object of the invention is to provide a method of higher accuracy then the known methods for indirect measurement of a patient's arterial tension.

Another object of the invention is to provide measurement of arterial tension in a moving patient.

One more object of the invention is to provide higher noise immunity of a device for pulse wave registration in indirect measurement of arterial tension.

The aforementioned objects are attained by the method of the invention for indirect measurement of arterial tension, wherein a compression cuff is applied to the surface of the patient's body, the pressure in the cuff is varied within a range which covers the systolic and diastolic values of the arterial tension, pulse waves produced by the releasing of the artery compressed by the cuff in the course of the aforesaid pressure variation therein are registered under the cuff on its area located past its midpoint as along the direction of the blood flow, and the pressure in the cuff is measured at the instants when pulse waves appear and disappear. In accordance with the invention, the instants when the pulse waves appear and disappear are registered by measuring the angle between the patient's body surface as displaced by the front of the passing pulse wave and the direction of propagation of such wave.

The objects of the invention are attained also by the device for registering the blood pulse waves, comprising a housing, a pellet movably mounted in the housing and having a contact surface, and a transducer converting the pellet motions into electric signals. In accordance with the invention, the pellet is mounted in the housing in a manner whereby it may oscillate angularly about a pivot axis. To this effect, the device is provided with a means for carrying out the pellet angular oscillations about a pivot axis which is parallel to the pellet contact surface and whose projection onto the pellet contact surface coincides with the axis of symmetry of said surface.

It is expedient that the means for effecting angular pellet oscillations be made as a double-bar articulated linkage, one of its bars being rigidly secured to the housing and the other bar, to the pellet, while the axis of rotation of the articulated linkage coincides with the pivot axis about which the pellet oscillates.

The transducer of the pellet angular oscillations into electric signals may be provided as a piezosensitive cell rigidly coupled to the housing and mechanically interacting with the pellet with a possibility of being flexed during angular oscillations of the pellet.

The transducer of the pellet angular oscillations into electric signals may also be made as an electromagnetic pair, containing a magnet and an induction coil of which one member may be fastened on the housing and the other, on the pellet.

It is also expedient that the means for effecting angular pellet oscillations be made as a flat spring located in a plane square with the pellet contact surface in such a manner that the axis of symmetry of the spring should coincide with the pellet pivot axis and that the ends of the spring be rigidly secured to the housing and the spring middle portion be rigidly coupled to the pellet.

The aforesaid flat spring is expedient to be made as a flat piezoelectric cell, whereby the spring may perform the function of a transducer converting the pellet angular oscillations into electric signals.

The method of the invention permits more accurate and reliable, then the heretofore known methods, measurement of the systolic and diastolic values of the patient's arterial blood tension, due to elimination of ambient noises, noises caused by pressure fluctuations in the cuff and by contractions of the patient's muscles. The method of the invention enables one to measure the arterial tension in the patient while the latter is in motion, which is the case, for example, when the patient is a sportsman or a newborn infant.

The method of the invention is instrumental in rendering the diagnosis more reliable and confident due to its capability of providing a dependable registration of the pulse wave alone against a background of ambient noises.

The device for registering the passing of the blood pulse waves made in accordance with the invention, features high noise immunity, since it is adapted to respond only to a change in the magnitude of the angle between the patient's body surface and the direction of propagation of the blood pulse waves and is insensitive to motions of the patient's body surface square with this surface which are caused by the most probable noises occurring in measuring the arterial tension (such as muscular contractions, pressure fluctuations in the cuff, ambient noises, etc.).

BRIEF DESCRIPTION OF THE DRAWINGS

For a fuller understanding of the invention, reference is had to the following description, taken in conjunction with the accompanying drawings, wherein.

DETAILED DESCRIPTION OF THE PREFERRED EMBODIMENTS

The method of indirect measurement of arterial tension, according to the invention, is illustrated in FIGS. 1, 2, 3, 4, 5 and 6.

Figure 1:
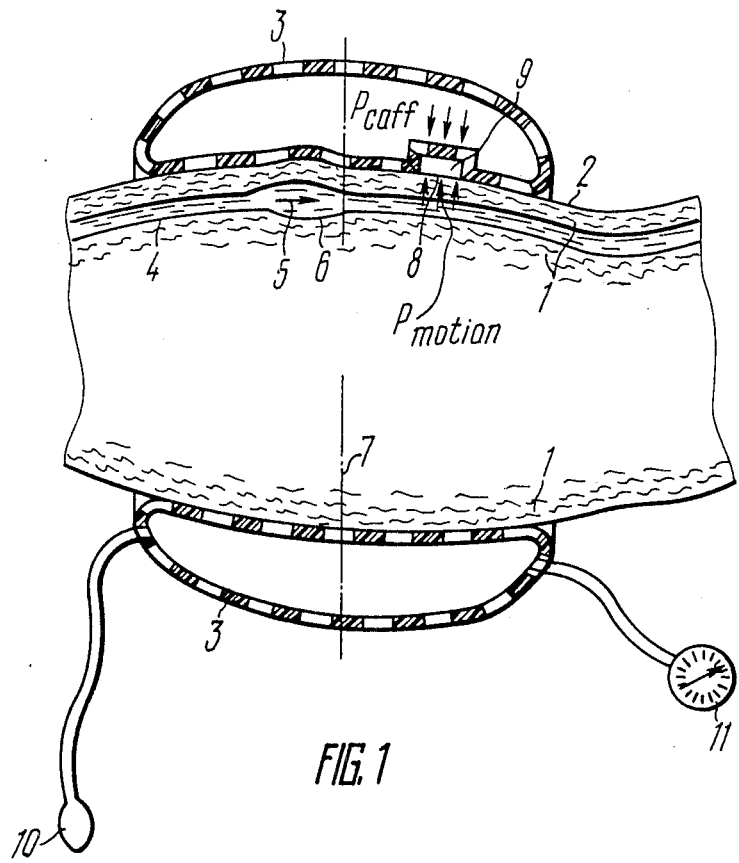
FIG. 1 shows the mutual arrangement of a patient's arm with an indicated artery, the compression cuff and the device for registering the passing of the pulse waves.

FIG. 1 illustrates a patient's arm 1 to a surface 2 of which a compression cuff 3 is applied. Passing along an artery 4 in a direction 5 is a blood pulse wave 6 caused by releasing the artery 4 at the instant when the arterial pressure value exceeds the gas pressure value in the compression cuff 3. The aforementioned blood pulse waves 6 occurs only in cases where the gas pressure in the cuff 3 is within the diastolic and systolic values of the arterial tension. Therefore, the systolic and diastolic values of the arterial tension can be judged by the values of the gas pressure in the cuff 3 when said pulse waves 6 appear and disappear. The blood pulse wave 6 passes under the cuff 3 as well, and is registered past a midpoint 7 of the cuff 3 as along the run of the wave 6 on an area 8 of the surface 2 located against the artery 4. A device 9 for registering the passing of the blood pulse wave 6 is placed for the purpose on the aforesaid area 8 of the patient's body surface 2. The passing of the blood wave 6 along the artery 4 is registered by measuring the angle made up by the area 8 of the patient's body surface 2 displaced by the front of the passing pulse wave 6, and the direction 5 of propagation of the blood pulse wave 6 along the artery 4. As it can be seen from FIG. 1 neither fluctuations of the gas pressure $P_{cuff}$ in the cuff 3 nor muscular efforts $P_{motion}$ of the patient can affect the aforesaid angle and hence the process of registering the passing of the blood pulse wave 6. The gas pressure in the cuff 3 is governed by a pump 10 and measured by a pressure gauge 11.

The passing of the blood pulse wave 6 under the preselected area 8 on the patient's body surface 2 and the effect of said wave on the registering device 9 placed on said area 8 are illustrated in FIGS. 2 through 5.

Figure 2:
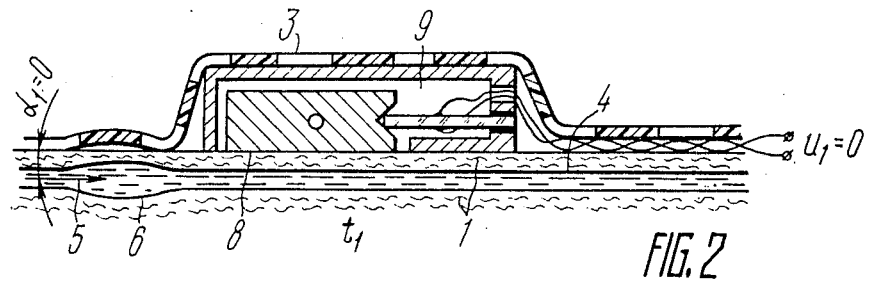
FIG. 2 shows a portion of the patient's body surface demonstrating the device for registering the passing of the blood pulse waves pressed against said portion by the compression cuff at the time instant $t_1$ when the pulse wave approaches the area of measurement.

FIG. 2 represents the instant of time $t_1$ when the blood pulse wave 6 has not yet reached the area 8 of the patient's body surface 2, and an angle $\alpha_1$ between said area 8 of the surface 2 and the direction 5 of propagation of the blood pulse wave equals zero.

Figure 3:
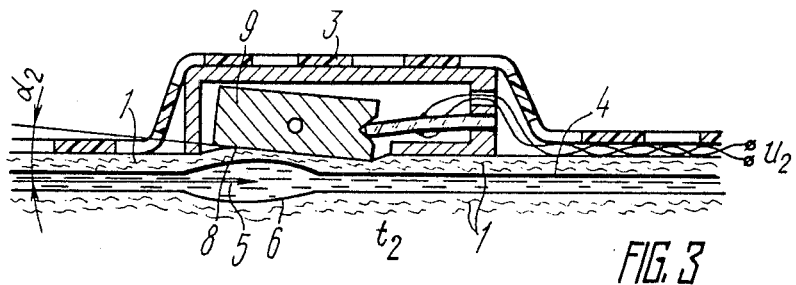
FIG. 3 is the same as in FIG. 2 at the time instant $t_2$ when the pulse wave interacts with the pellet with its front.

FIG. 3 shows the instant of time $t_2$ (at which the pulse wave appears) when the blood pulse wave 6 has produced an angle $\alpha_2$ other than zero, defined by the area 8 of the surface 2 and the direction 5 of propagation of the blood pulse wave 6.

Figure 4:
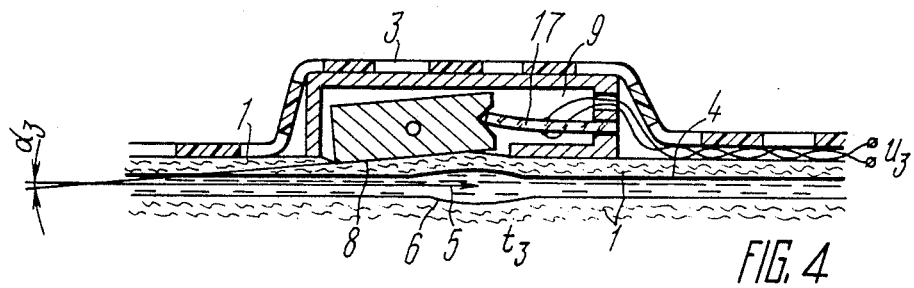
FIG. 4 is the same as in FIG. 2 at the time instant $t_3$ when the pulse wave interacts with the pellet with its back.

FIG. 4 illustrates further propagation of the blood pulse wave along the artery 4 at the instant of time $t_3$ when the wave 6 interacts with the device with its back (trailing edge) with the resultant sign reversal of the angle $\alpha_3$ compared to the angle $\alpha_2$.

Figure 5:
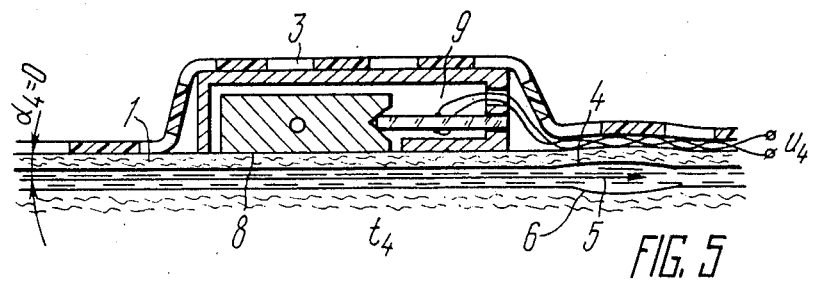
FIG. 5 is the same as in FIG. 2 at the time instant $t_4$ when the pulse wave has come beyond the limits of the area of measurement.

FIG. 5 demonstrates the instant of time $t_4$ when the blood pulse wave 6 has already come off the area 8 of measurement and an angle $\alpha_4$ between the surface area 8 and the direction 5 of propagation of the wave 6 has become zero once again.

Figure 6:
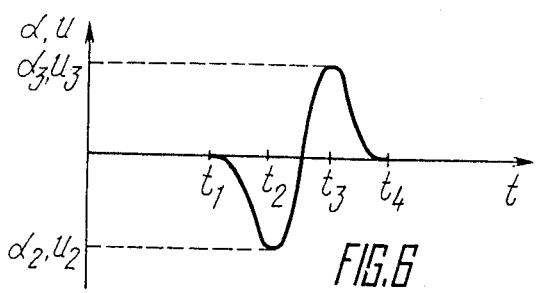
FIG. 6 shows the graphic function of transducer output electric signal (U) vs time (t)

Thus, the passing of the pulse wave 6 under the area 8 of measurement causes a pulsatory change of the aforesaid angle and hence of the magnitude of a signal U at the output of the device 9, which is illustrated in FIG. 6.

The systolic value of the arterial pressure is registered against the appearance of the initial signal at the output of the device 9. As further decompression proceeds the device 9 will generate electric signals in response to each passing of the pulse waves until the pressure becomes equal to the diastolic value. With the pressure in the cuff 3 below the diastolic value no electric signals are generated by the device 9. The instant when the last signal arrives from the device 9 (that is, when the pulse waves disappear) corresponds to the diastolic value of the patient's arterial tension.

The device 9 for registering the passing of the pulse waves in indirect measurement of arterial tension comprises a pellet 13 accommodated in a housing 12 (FIGS. 7, 8) and capable of angular oscillatory motion about a pivot axis 14, which is parallel to a contact surface 15 of the pellet 13 and the projection of said pivot axis onto the contact surface 15 coincides with the axis of symmetry of said surface.

Figure 7:
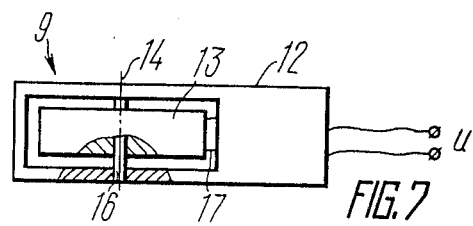
FIG. 7 is a plan view, partially in section, of an embodiment of the device for registering the passing of the pulse waves featuring an articulately suspended pellet and a piezosensitive transducer.
Figure 8:
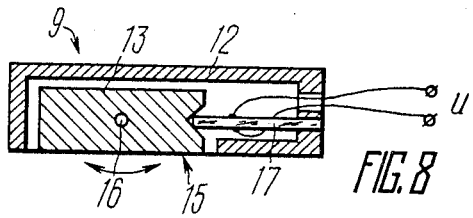
FIG. 8 is a sectional view of the embodiment of FIG. 7.

The device 9 is also provided with a means for effecting angular oscillations of the pellet about the pivot axis 14. In the embodiment of the device as illustrated in FIGS. 7 and 8, said means is made as an articulated linkage, one of whose members, that is, a round bar 16 is rigidly secured with its ends to the housing 12, while the other member of the articulated linkage is shaped as a holder made integral with the pellet 13. The axis of the bar 16 (that is, the axis of rotation of the linkage) coincides with the pivot axis 14 of the pellet 13.

A piezosensitive cell 17 is employed as a transducer converting the angular oscillations of the pellet 13 into electric signal U. The cell 17 is rigidly coupled to the housing 12 and is adapted to mechanically interact with the pellet 13 with a possibility of being flexed during angular oscillations of the pellet 13 about the pivot axis 14.

Figure 9:
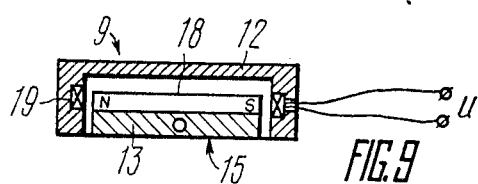
FIG. 9 is a similar view as in FIG. 7 with the transducer made as an electromagnetic pair.

FIG. 9 illustrates an alternative embodiment of the device 9, which differs from the embodiment shown in FIGS. 7 and 8 in the type of the transducer converting the angular oscillations of the pellet 13 into an electric signal U. The said transducer is made as an electromagnetic pair, comprising a magnet 18 and an induction coil 19. One of the components of this pair (the magnet 18 in this particular case) is located on the pellet 13 and the other component, the induction coil 19 is situated in the housing 12.

Figure 10:
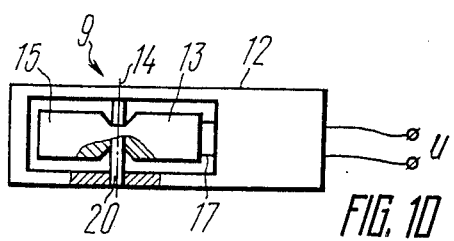
FIG. 10 is a similar view as in FIG. 7 showing the pellet suspended on a flat spring.
Figure 11:
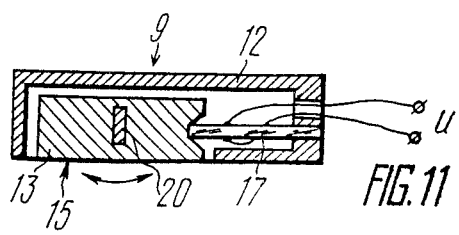
FIG. 11 is a sectional view of the embodiment of FIG. 10.

FIGS. 10 and 11 show one more embodiment of the device 9, wherein as distinct from the embodiment of FIGS. 7 and 8, the means for effecting angular oscillations of the pellet 13 about the pivot axis 14 is made as a flat spring 20 whose axis of symmetry coincides with the pivot axis 14 of the pellet 13. Two opposite ends of the flat spring 20 are rigidly affixed to the housing 12, while the middle portion of this spring is rigidly attached to the pellet 13. The plane in which the flat spring 20 is located, is square with the contact surface 15 of the pellet 13 and intersects it along the axis of symmetry of the contact surface 15. The aforedescribed embodiment of suspension of the pellet 13 in the housing 12 enables the pellet 13 to oscillate about the pivot axis 14 by virtue of twisting the flat spring 20.

Figure 12:
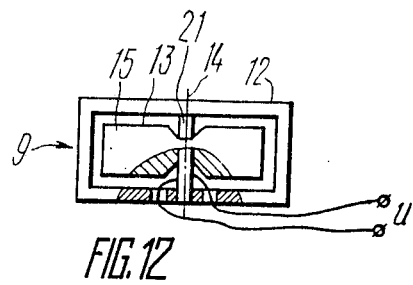
FIG. 12 is a similar view as in FIG. 10 with the flat spring serving at the same time as a transducer.

Still one more embodiment of the device 9 represented in FIG. 12 differs from the embodiment of FIGS. 10 and 11 in that the means for imparting angular oscillations to the pellet is made as a flat piezosensitive cell 21 which serves simultaneously as a transducer converting angular pellet oscillations into electric signals and as a flat spring.

FIGS. 13, 14, 15, 16 represent some embodiments of the flat piezosensitive cell 21 capable of producing electric signal U when twisted.

Figure 13:
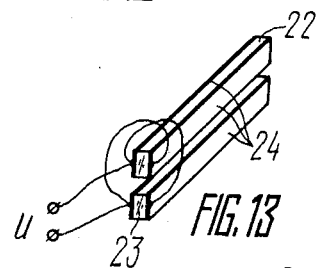
FIGS. 13, 14, 15 and 16 are the embodiments of the flat spring performing at the same time the function of a transducer converting the pellet oscillations into electric signals.

FIG. 13 illustrates a flat piezosensitive cell made as two parallel piezoelectric crystal wafers 22 and 23 with parallel-connected current-conducting plates 24.

Figure 14:
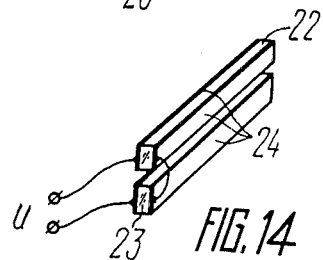

FIG. 14 shows the embodiment of FIG. 13, wherein, as distinct from the latter, the current-conducting plates 24 are series-connected.

Figure 15:
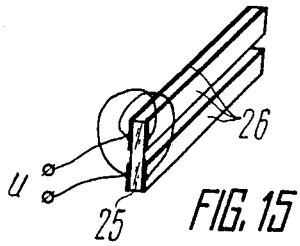

FIG. 15 depicts a flat piezosensitive cell established on a single piezoelectric crystal wafer 25 with two pairs of parallel-connected current-conducting plates 26.

Figure 16:
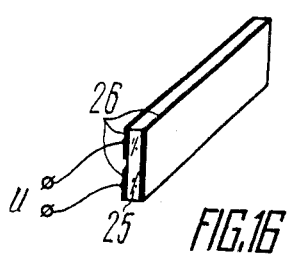

In FIG. 16 the current-conducting plates 26 are series-connected.

In accordance with the invention, the patient's arterial tension is measured by placing the device 9 for registering the passing of the pulse waves on the surface of the patient's body, e.g., on the arm, in such a manner that the contact surface 15 should fit to the patient's body surface 2. Then the compression cuff 3 is applied above the device 9 taking care to see that the device 9 should be located past the midpoint 7 of the cuff 3 as along the flow of blood. Next an excess air pressure is built up in the cuff 3, said pressure exceeding the systolic value of the patient's blood pressure. The pressure in the cuff 3 is then monitored under slow-rate decompression conditions against, for example, a pressure gauge. In this case, an initial pulse wave (FIG. 3) will pass at a pressure in the cuff 3 equal to the systolic value of the arterial pressure effective on the patient's body area 8 under measurement and will cause a change in the angle between the body surface 2 and the direction of propagation of said wave from $\alpha_2$ and $\alpha_3$.

As a result, the pellet 13 contacting the patient's body surface 2, will oscillate about the pivot axis 14. This in turn causes electric signal U to appear at the output of the transducer 17 due to mechanical linkage of the pellet 13 and said transducer.

Further decompression results in appearing an electric signal at the output of the device 9, similar to that shown in FIG. 6 until the pressure in the cuff 3 becomes equal to the diastolic value. As soon as the pressure in the cuff drops below the diastolic value, no pulse waves are passing and the signal at the output of the device 9 becomes equal to zero. The instant when the last signal arrives from the device 9 corresponds to the diastolic value of the patient's arterial pressure.

When pressure fluctuations occur in the cuff 3, or muscular contractions of the patient's body arise under the cuff 3, some forces are developed that act equally upon the entire contact surface 15 of the pellet 13. Inasmuch as the projection of the horizontal pivot axis 14 coincides with the axis of symmetry of the contact surface 15 of the pellet 13, the forces exerted upon the contact surface 15 are divided by the said axis of symmetry and thus balance each other so that they do not cause the pellet 13 to rotate about the pivot axis 14. That is, these forces neither create angular oscillations of the pellet 13 nor generate an electric signal via the device 9.

The embodiments of the device for registering the passing of the pulse waves as shown in FIGS. 9, 10, 11 and 12, function in the same manner as the device illustrated in FIGS. 7 and 8.

What is claimed is:

1. A device for registering the passing of blood pulse waves in indirect measurement of arterial pressure of a patient, said device comprising
   a housing;
   a pellet accommodated in said housing, said pellet being mounted for angular oscillation about a pivot axis, said pellet having a symmetrical contact surface adapted to interact with the surface of the body of the patient at said contact surface thereof, said pivot axis being substantially parallel to said contact surface of said pellet, the projection of said pivot axis onto said contact surface coinciding with an axis of symmetry of said surface;
   an articulated linkage for effecting angular oscillations of said pellet about said pivot axis, said articulated linkage having a pivot shaft coupled to said pellet and having an axis coinciding with said pivot axis, said pivot shaft being connected to said housing such that said axis of said pivot shaft is fixed with respect to said housing; and
   transducer means for converting said angular oscillations of said pellet into electric signals.

2. A device as claimed in claim 1 wherein said transducer means comprises a piezosensitive cell rigidly affixed to said housing and mechanically interacting with said pellet, said piezosensitive cell extending in a direction between said housing and said pellet substantially perpendicular to said pivot axis, said transducer means being mounted for flexure during said angular oscillations of said pellet about said pivot axis.

3. A device as claimed in claim 1, wherein said transducer means comprises an electromagnetic pair including a magnet and an induction coil, one of the components of said electromagnetic pair being affixed to said pellet and the other of the components of said electromagnetic pair being secured to said housing.

4. The device of claim 3, wherein said magnet is affixed to said pellet and said induction coil is affixed to said housing.

5. The device of claim 1, additionally comprising
   a compression cuff disposed about said housing, with said housing offset from a midpoint of said cuff,
   said device adapted to be applied to the surface of the body of the patient adjacent a blood vessel, with said housing situated downstream of the midpoint of said cuff in the direction of blood flow.

6. The device of claim 1, wherein said pivot shaft extends through said pellet and is connected to said housing at opposite ends thereof.

7. The device of claim 6, wherein said pivot shaft is rigidly connected to said housing at the opposite ends thereof.

8. A device for registering the passing of blood pulse waves in indirect measurement of arterial pressure of a patient, said device comprising
   a housing;
   a pellet accommodated in said housing, said pellet being mounted for angular oscillation about a pivot axis, said pellet having a symmetrical contact surface adapted to interact with the surface of the body of the patient at the contact surface thereof, said pivot axis being substantially parallel to said contact surface of said pellet, the projection of said pivot axis onto said contact surface coinciding with an axis or symmetry of said surface;
   a flat spring having an axis of symmetry coinciding with said pivot axis, said flat spring being located in a plane substantially perpendicular with said contact surface of said pellet, said flat spring having two spaced opposite ends rigidly secured to said housing and a middle portion rigidly attached to said pellet; and
   transducer means for converting said angular oscillations of said pellet into electric signals.

9. The device of claim 8, wherein said transducer means comprises a piezosensitive cell rigidly affixed to said housing and mechanically interacting with said pellet, said piezosensitive cell extending in a direction between said housing and said pellet substantially perpendicular to said pivot axis, said transducer means being mounted for flexure during said angular oscillations of said pellet about said pivot axis.

10. The device of claim 8, additionally comprising
    a compression cuff disposed about said housing, with said housing offset from a midpoint of said cuff,
    said device adapted to be applied to the surface of the body of the patient adjacent a blood vessel, with said housing situated downstream of the midpoint of said cuff in the direction of blood flow.

11. A device for registering the passing of blood pulse waves in indirect measurement of arterial pressure or a patient, said device comprising a housing;

a pellet accommodated in said housing, said pellet mounted for angular oscillation about a pivot axis, said pellet having a symmetrical contact surface adapted to interact with the surface of the body of the patient at said contact surface thereof, said pivot axis being substantially parallel to said contact surface of said pellet, the projection of said pivot axis onto said contact surface coinciding with an axis of symmetry of said surface;

a flat piezosensitive cell means for effecting angular oscillations of said pellet about said pivot axis, said cell means being rigidly affixed to said housing at opposite ends thereof, and having an axis of symmetry coinciding with said pivot axis and a middle portion mechanically interacting with said pellet;

said cell means also constituting transducer means for converting said angular oscillations of said pellet into electric signals.

12. The device of claim 10 additionally comprising a compression cuff disposed about said housing, with said housing offset from a midpoint of said cuff, said device adapted to be applied to the surface of the body of the patient adjacent a blood vessel, with said housing situated downstream of the midpoint of said cuff in the direction of blood flow.

* * * * *